United States Patent [19]

Merianos

[11] Patent Number: 5,216,030
[45] Date of Patent: Jun. 1, 1993

[54] ANTIMICROBIAL, LOW TOXICITY, BLEND COMPOSITION OF BIS-QUATERNARY AMMONIUM COMPOUNDS AND POLYVINYLPYRROLIDONE

[75] Inventor: John J. Merianos, Middletown, N.J.

[73] Assignee: ISP Investments Inc., Wilmington, Del.

[21] Appl. No.: 772,409

[22] Filed: Oct. 7, 1991

[51] Int. Cl.$^5$ ............................................. A61K 31/13
[52] U.S. Cl. ................................... 514/668; 514/846; 514/845; 424/72
[58] Field of Search ....................... 514/845, 846, 668; 424/72

[56] References Cited

PUBLICATIONS

*Pharmaceutical Dosage Forms: Tablets* Leiberman, et al., editors vol. 3, pp. 92–94 (1982) Marcel Dekkor, Inc.; N.Y.

*Primary Examiner*—Frederick E. Waddell
*Assistant Examiner*—F. Tsung
*Attorney, Agent, or Firm*—Walter Katz; Marilyn J. Maue; Joshua J. Ward

[57] ABSTRACT

An antimicrobial, low toxicity blend composition of several bis-quaternary ammonium compounds of defined structure, and in defined amounts of the composition, and polyvinylpyrrolidone, is described herein.

5 Claims, No Drawings

ANTIMICROBIAL, LOW TOXICITY, BLEND COMPOSITION OF BIS-QUATERNARY AMMONIUM COMPOUNDS AND POLYVINYLPYRROLIDONE

BACKGROUND OF THE INVENTION

1. Field of the Invention

This invention relates to antimicrobial compounds, and, more particularly, to a blend of such compounds and polyvinylpyrrolidone having enhanced antimicrobial activity, excellent solubility in water, and low irritation to the user.

2. Description of the Prior Art

Bisquaternary ammonium compounds, such as acrylic alkyleneoxylated bisquaternary ammonium compounds, have been formulated into shampoo and cosmetic cleansing compounds as mildness additives for the detergents therein; see U.S. Pat. No. 4,110,263. However, for these and other applications, where the antimicrobial properties of such compounds are utilized, it is desired to provide compositions containing such compounds having enhanced antimicrobial activity.

Accordingly, it is an object of the present invention to provide a blend of bisquaternary ammonium compounds and a coprecipitant therewith having enhanced antimicrobial activity, excellent solubility in water and low irritation to the user.

These and other objects and features of the invention will be made apparent from the following description herein.

SUMMARY OF THE INVENTION

What is provided herein is a defined antimicrobial blend composition of bis-quaternary ammonium compounds selected from those represented by the

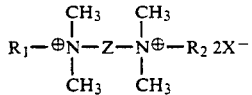

in which Z is

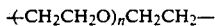

where n is 1 (H Blend) or 2 (D Blend); or
—$CH_2CH=CH-CH_2$— (L Blend); and
$R_1$ and $R_2$ are independently $C_{12}$ or $C_{14}$-alkyl;
$X^-$ is a halogen such as Cl, Br or I; and in the weight ratio of about
25% of the compound where both $R_1$ and $R_2$ are $C_{12}$-alkyl;
50% of the compound where $R_1$ is $C_{12}$-alkyl and $R_2$ is $C_{14}$-alkyl; and
25% of the compound where both $R_1$ and $R_2$ are $C_{14}$-alkyl;
the stated weight percents being ±20%; and polyvinylpyrrolidone (PVP) as a coprecipitate or in admixture therewith.

The thus-defined blend composition exhibits enhanced antimicrobial activity, and is less toxic, as compared to the individual compounds in the composition; and has increased water solubility and less irritation to the user as compared to the blend without polyvinylpyrrolidone.

In the preferred embodiment of the invention, Z is

and n is 2.

DETAILED DESCRIPTION OF THE INVENTION

The bis-quaternary ammonium compounds used to prepare the blend composition of the invention are made by reacting one mole of a dihalo compound selected from:

$XCH_2CH_2OCH_2CH_2X$, $XCH_2CH_2OCH_2CH_2OCH_2CH_2X$ and $XCH_2CH=CHCH_2X$;

where X is a halide such as Cl, Br and I, with 2 moles of dodecyldimethyl amine, tetradecyldimethylamine or predetermined mixtures thereof.

A typical reaction is the following:

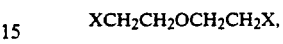      (1 mole)

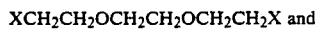

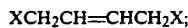

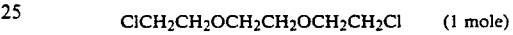

A reaction mixture of one mole of dodecyldimethylamine, one mole of the tetradecyldimethylamine and one mole of the dichloro compound will provide the blend composition D as a mixture of three individual compounds A, B and C, in defined amounts of each, as shown below.

BLEND COMPOSITION D

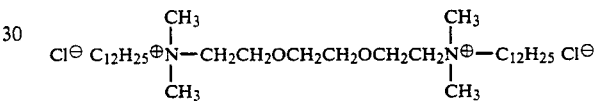

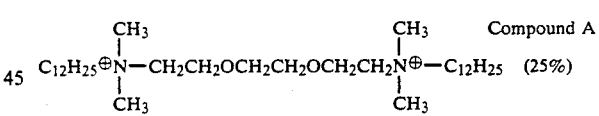

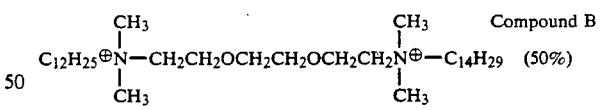

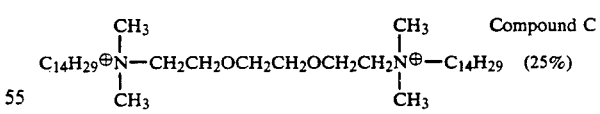

where the stated percentages are ±20%, usually about ±5–10%. Of course, by varying the relative amounts of starting materials, a blend of different percentages of the individual compounds may be obtained.

The blend composition with polyvinylpyrrolidone usually is prepared by reacting a dilute solution of the blend composition in alcohol or water, preferably methanol, with a dilute solution of the bisquat blend composition in the same solvent, and removing the solvent to form the desired coprecipitate solid product. More particularly, the blend coprecipitate compositions of the invention are prepared by refluxing the selected dichloro compound, the amines, and an alkali metal halide, in alcoholic solution, removing the solvent, precipitating the blend of bisquats in an organic solvent in substantially quantitative yield, and reacting a solution of the thus-prepared bisquat in methanol or water with a solution of soluble polyvinylpyrrolidone in the same solvent, and removing the solvent under reduced pressure to form the solid coprecipitate product.

These blend compositions with polyvinylpyrrolidone exhibit an enhanced antimicrobial activity and reduced toxicity as compared to the individual compounds therein. Furthermore, they show excellent solubility in water, and less irritation to the user, as compared to the blend composition itself, that is, without polyvinylpyrrolidone.

The antimicrobial compositions of the invention may be used as such, or, preferably, admixed with an inactive or inert component to prepare pharmaceutical formulations such as powders, solutions, lotions, suspensions and the like. Typical additives include water, alcohols, starch, etc. Other active ingredients may be included if desired.

While the coprecipitate form is favored, mixtures of the blend composition and polyvinylpyrrolidone may be used as well.

Typical antimicrobial activities, represented by their Minimum Inhibitory Concentration (MIC), against E.-Coli, a gram negative microorganism, is presented in the Table below for both the individual compounds in blend composition D and the D, H and L blend compositions with polyvinylpyrrolidone at different relative amounts of the compounds therein (as measured in a 10% active solution).

TABLE

| Compound or Blend | MIC |
|---|---|
| A compound in D blend | 100> |
| C compound in D blend | 125 |
| B compound in D blend | 50 |
| D coprecipitate of 25A/50B/25C composition with polyvinylpyrrolidone (50:50) | 5 |
| D coprecipitate of 40A/20B/40C composition with polyvinylpyrrolidone (50:50) | 35 |
| D coprecipitate of 33A/33B/33C composition with polyvinylpyrrolidone (50:50) | 30 |
| D coprecipitate of 10A/80B/10C composition with polyvinylpyrrolidone (50:50) | 25 |
| H coprecipitate of 25A/50B/25C composition with polyvinylpyrrolidone (50:50) | 15 |
| L coprecipitate of 25A/50B/25C composition with polyvinylpyrrolidone (50:50) | 5 |

The MIC values of the blend-PVP coprecipitate compositions in the TABLE are up to 25 times more favorable than the individual compounds in the blend.

The compositions of the invention also have increased water solubility than blends without PVP.

The LD$_{50}$ toxicity of the D blend-PVP compositions above also is reduced by a factor of 5-6 as compared to the individual compounds in the blend, furthermore they exhibit a substantially reduced irritation to the skin as compared to the individual compounds or the blend without PVP.

The invention will now be illustrated by the following example.

EXAMPLE

Preparation of Blend D-PVP Composition

1. A reaction solution of:
1,2-bis(2-chloroethoxy) ethane 37.5 g., 0.2 mole;
Dodecyldimethylamine 42.6 g., 0.2 mole;
Tetradecyldimethylamine 48.4 g., 0.2 mole;
Potassium Iodide 5 g.; and
Methanol 200 g.,
was mixed well and heated to 90-100° C. for 12 hours. Then the solvent was removed to give a heavy syrupy residue which was treated with acetone to precipitate out the bisquats of the D blend composition in a yield of at least 95%. The blend composition comprised 25% by weight of A, 50% by weight of B and 25% by weight of C compounds.

2. A 10% by weight solution of PVP-CI in methanol was mixed with a 10% solution of the bisquat prepared above in methanol. The solvent then was removed under reduced pressure whereupon a solid coprecipitate was formed which analyzed 50% by weight active D bisquat blend and 50% by weight PVP.

While the invention has been described with particular reference to certain embodiments thereof, it will be understood that changes and modifications may be made which are within the skill of the art. Accordingly, it is intended to be bound only by the following claims, in which:

What is claimed is:

1. An antimicrobial, low toxicity composition of a blend of bis-quaternary ammonium compounds having the formula:

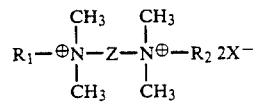

in which Z is

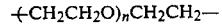

where n is 2;
and
$R_1$ and $R_2$ are independently $C_{12}$ or $C_{14}$-alkyl;
$X^-$ is a halogen such as Cl, Br or I; and in the weight ratio of
25% by weight of the compound where both $R_1$ and $R_2$ are $C_{12}$-alkyl;
50% by weight of the compound where $R_1$ is $C_{12}$-alkyl and $R_2$ is $C_{14}$-alkyl; and
25% by weight of the compound where both $R_1$ and $R_2$ are $C_{14}$-alkyl;
the stated weight percents being ±20%; and polyvinylpyrrolidone (PVP), as a coprecipitate or in admixture therewith.

2. A composition according to claim 1 wherein said percentages are ±5-10%.

3. A composition according to claim 1 wherein said stated percentages are ±5-10%.

4. A composition according to claim 1 which includes an inert component.

5. A composition according to claim 1 wherein said polyvinylpyrrolidone is coprecipitated with the blend of said bis-quaternary compounds.

* * * * *